United States Patent [19]

Darst et al.

[11] Patent Number: 5,235,094

[45] Date of Patent: Aug. 10, 1993

[54] PROCESS FOR PREPARATION OF HALOGINATED ESTERS

[75] Inventors: Kevin P. Darst; Marius W. Sorenson, both of Lake Jackson, Tex.

[73] Assignee: The Dow Chemical Company, Midland, Mich.

[21] Appl. No.: 806,937

[22] Filed: Dec. 11, 1991

[51] Int. Cl.⁵ .............................................. C07C 69/66
[52] U.S. Cl. .................................... 560/184; 560/247
[58] Field of Search .......................................... 560/184

[56] References Cited

U.S. PATENT DOCUMENTS

| | | | |
|---|---|---|---|
| 2,988,537 | 6/1961 | Wiley | 260/67 |
| 4,292,449 | 9/1981 | Krespan | 568/649 |
| 4,349,650 | 9/1982 | Krespan | 526/243 |
| 4,474,700 | 10/1984 | Krespan | 260/349 |
| 4,576,752 | 3/1986 | Krespan | 260/349 |

Primary Examiner—JosAU/e/ G. Dees
Assistant Examiner—Porfirio Nazario
Attorney, Agent, or Firm—John A. Langworthy

[57] ABSTRACT

A halogenated ester is prepared by addition of a halogenated nucleophile to a diester at a temperature less than 15° C. but greater than −25° C.

13 Claims, No Drawings

PROCESS FOR PREPARATION OF HALOGINATED ESTERS

FIELD OF THE INVENTION

This invention relates to a process for the preparation of halogenated esters.

BACKGROUND OF THE INVENTION

It is often advantageous to prepare a halogenated ester by addition of a halogenated nucleophile to an alcohol-derived diester. If only one of the oxyanionic alcohol residues is displaced from the carbonyl carbon of the diester by the halogenated nucleophile, the desired ester results. If, however, both oxyanionic residues are displaced, a ketone byproduct results instead. A mixture of the desired ester and the ketone byproduct is usually obtained from this type of addition reaction.

In Wiley, U.S. Pat. No. 2,988,537, a method is described in which, in the presence of an alkoxide ion, a halogenated, ethylenically unsaturated olefin can be added to either a mono- or diester or a carboxamide. The results of the experimental work disclosed in Wiley recognize that when such addition is made to a carbonate ester, a mixture is obtained of an ester to which one equivalent of halogenated olefin has been added, and a ketone to which two equivalents of the olefin have been added. However, there is no indication in Wiley that one of those products is sought in preference to the other. The method of Wiley consequently does not offer any guidance as to how ester synthesis by halogenated olefin addition can be operated to obtain a desirably high, and preferably maximum, yield of the ester while holding the quantity of the ketone to as low a level as possible.

It would consequently be desirable to have a process which would allow nucleophilic addition of a halogenated olefin to a diester with a resulting preferential yield of a high ratio of ester product to ketone byproduct.

SUMMARY OF THE INVENTION

In one aspect, this invention involves a process for preparing a halogenated ester by (a) contacting a reaction mixture of a nucleophile precursor and a diester with a halogenated, ethylenically unsaturated olefin at a temperature less than 15° C. but greater than about −25° C., (b) contacting an acid with said reaction mixture, and (c) recovering a halogenated ester from said reaction mixture.

In another aspect, this invention involves a process for preparing a halogenated ester comprising (a) contacting (i) a reaction mixture of a nucleophile precursor and a diester with (ii) less than about 0.99 mole but at least about 0.89 mole of a halogenated, ethylenically unsaturated olefin per mole of nucleophile precursor present in said reaction mixture, (b) contacting an acid with said reaction mixture, and (c) recovering a halogenated ester from said reaction mixture.

The process of this invention yields a product which contains a desirably high ratio of the halogenated ester as compared to the halogenated ketone.

By the process of this invention, halogenated esters are prepared which may be converted to a dicarbonyl compound. Such a dicarbonyl compound may be used to prepare unsaturated ethers which may, in turn, be copolymerized with other unsaturated, halogenated monomers (such as tetrafluoroethylene) to obtain polymers suitable for fabrication into films, membranes and other finished goods.

DETAILED DESCRIPTION OF THE INVENTION

In one method of practicing this invention, a slurry containing a nucleophile precursor and a diester, such as a carbonate ester, is formed in an inert organic solvent (inert in this context meaning non-reactive with any of the reactants or products). In the slurry, the nucleophile precursor (such as an alkali metal alkoxide) forms an ion capable of attacking the carbonyl carbon of the diester. It is preferred that moisture be excluded from the reagents in the slurry, and this may be accomplished, for example, by first forming a solution of the diester and the solvent and then drying it before the nucleophile precursor is added to form a reaction mixture. To dry the solution, it may, for example, be circulated through a 4 Angstrom molecular sieve bed. A water content in the diester/solvent solution of no more than about 500 weight parts per million, by weight, is preferred. Moisture should also be excluded from the reaction apparatus by appropriate drying techniques. It is also preferred that air be excluded from the reaction, and this may be accomplished, for example, by running the reaction under a nitrogen atmosphere.

After a nucleophile precursor is added to form a reaction mixture, the mixture is cooled to a selected temperature below 15° C., preferably below about 10° C. and more preferably below about 0° C., and yet above about −25° C., preferably above about −15° C. and more preferably above about −10° C., as well. With stirring, a halogenated, ethylenically unsaturated olefin is metered into the reaction vessel and contacted with the mixture. The nucleophile adds first to the double bond of the halogenated olefin and then attacks the carbonyl carbon of the diester.

At the beginning of and during the course of this addition reaction, the selected temperature within the range specified above is maintained. Since the reaction is exothermic, cooling for such temperature maintenance is accomplished by cooling apparatus as well as by reducing the rate of flow of the halogenated olefin into the reaction vessel as needed to regulate the temperature of the reaction mixture. The flow rate of the halogenated olefin may also be reduced if needed to prevent the pressure within the reaction vessel from exceeding safe limits. A flow rate for the halogenated olefin of about 0.5 mole to about 1 mole per hour is typical on the laboratory scale.

It is preferred that the amount of halogenated olefin fed to the reaction mixture be less than about 99 percent of, and preferably less than about 95 percent of, and yet at least about 89 percent of, and preferably at least about 93 percent of, the stoichiometric amount needed to react with the nucleophile precursor. It is particularly preferred that the calculation of such amount of halogenated olefin to be utilized be made based on the purity of the nucleophile precursor. For example, one mole of a nucleophile precursor which is only 98 percent pure would represent, in terms of stoichiometric equivalence, only 0.98 mole of 100 percent pure nucleophile precursor.

The reaction has at this point created an intermediate in which oxygen double-bonded to the carbonyl carbon carries a total negative charge by reason of addition to the carbonyl carbon of the diester of one or two equivalents of the halogenated nucleophile created first by reaction of the original nucleophile with the ethylenically unsaturated halogenated olefin. When two equivalents of halogenated nucleophile have added to the carbonyl carbon, one of the oxyanionic alcohol residues will have already been eliminated from the diester. Completion of formation of these mono- and bis-addition intermediates usually occurs, on the laboratory scale, within about 0.5 hour to about 2 hours after feed of the halogenated olefin is stopped.

The reactants need not necessarily be contacted in the order or by the means as described above. For example, in a case where all reactants can be fed in liquid form, it may be desirable to admix them simultaneously.

After the feed of halogenated olefin is concluded, the pH of the reaction mixture is adjusted in a neutralization step by addition thereto with agitation of an anhydrous acid strong enough to cause elimination of a remaining oxyanionic alcohol residue from the carbonyl carbon of the diester. It is preferred that, during acid addition, the temperature of the reaction mixture be below 15° C., and more preferably be at the selected level within the ranges set forth above. Temperature control for such purpose may be accomplished by reducing the rate of acid addition or by use of cooling apparatus. Completion of the step of elimination of a remaining oxyanionic residue usually occurs within about 0.1 hour to about 1 hour, if not immediately.

After completion of the elimination step to form the desired mono-ester product, which also results in formation of the ketone byproduct from bis addition of the nucleophilic halogenated olefin, the product is recovered by conventional means such as removing the salt in a filter, centrifuge or aqueous wash, and then distilling the filtrate. If a filter or centrifuge is used, the mesh or screen opening may, for example, be no more than about 1 micron, or about 1 to about 2 microns. The ketone byproduct is, of course, passed through these recovery steps along with the ester product.

The reactants described above may be used in the process of this invention in number of moles per mole of nucleophile precursor as follows:

(i) halogenated olefin: 1.0, preferably less than about 0.99, and more preferably less than about 0.95, and yet at least about 0.89, and more preferably at least about 0.93;
(ii) diester: about 2.0 to about 3.0, and preferably about 2.0 to about 2.2;
(iii) solvent: about 0.8 to about 2.0, and preferably about 1.0 to about 1.2; and
(iv) acid: about 1.0.

A nucleophile precursor, from which an ion capable of attacking the carbonyl carbon of the diester may be derived, can be suitably obtained, for example, from compounds described generally by the formula M—O—Z, where M is an alkali metal such as lithium, sodium, potassium or cesium or an alkaline earth metal such as magnesium or calcium; and Z is a linear, branched or cyclic alkyl or alkylene radical containing 1 to 18 carbon atoms, preferably 1-10 carbon atoms, more preferably 1 to 6 carbon atoms, and most preferably 1-4 carbon atoms, and optionally containing halogen (such as chlorine, fluorine or bromine) substituents. Representative examples of Z include methyl, ethyl, isopropyl, isobutyl, isopentyl, neopentyl, pentyl, cyclopentyl, hexyl, cyclohexyl, octyl, cyclooctyl, nonyl, decyl radicals, and the like, each optionally containing halogen substituents. An example of a preferred nucleophile is an alkoxide ion derived from sodium methoxide (sodium methylate). Sodium methoxide is commercially available or may be made, for example, by either reacting molten sodium with methanol or by reacting methanol with sodium amalgam obtained from the electrolysis of brine.

Halogenated olefin compounds which may be advantageously used for addition to a diester in the process of this invention can be described generally by the formula $CX_2=CX_2$, where each X is independently hydrogen, fluorine, chlorine, bromine or iodine, provided that at least one X must be fluorine. An example of a preferred halogenated olefin is tetrafluoroethylene, which is available commercially or may be made by reacting hydrogen fluoride and chloroform to give chlorodifluoromethane, which is then pyrolyzed in a noncatalytic gas-phase reaction at atmospheric or reduced pressure, usually at about 590°-900° C.

Representative diesters which are useful in the process of this invention may include carbonate esters (carbonic acid esters) such as those described generally by the formula:

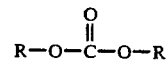

where each R is independently a linear, branched or cyclic alkyl or alkylene radical, or an aryl or arylene radical, containing 1 to 18 carbon atoms, preferably 1-10 carbon atoms, and more preferably 1 to 6 carbon atoms, and optionally containing halogen (such as chlorine, fluorine or bromine) substituents. Representative examples of R include methyl, ethyl, isopropyl, isobutyl, isopentyl, neopentyl, pentyl, cyclopentyl, hexyl, cyclohexyl, octyl, cyclooctyl, nonyl, decyl, benzyl, tolyl, xylyl and naphthyl radicals, and the like, each optionally containing halogen substituents. An example of a preferred diester is dimethylcarbonate (where each R is $CH_3$), which is available commercially or may be prepared by reacting carbon monoxide, oxygen and methanol at about 90° C. and about 10 MPa or less, using a cuprous chloride catalyst.

For performing the neutralization step, organic acids such as acetic, formic or propionic acid can be used, however a mineral acid such as hydrochloric, sulfuric, phosphoric, hydrobromic, sulfonic, or nitric acid, and the like, is preferred. Suitable non-reactive solvents in which to run the reaction include diethyl ether, tetrahydrofuran and 1-2,dimethoxyethane.

The desired ester product formed from the reactants described above may be described by formula as follows:

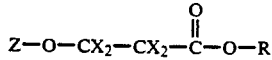

where R, X and Z are as set forth above.

As a particular example, when tetrafluoroethylene ($CF_2=CF_2$) is added to a slurry of sodium methoxide ($NaOCH_3$) and dimethyl carbonate [$(CH_3O)_2C=O$] in tetrahydrofuran, and the resulting intermediates are neutralized with HCl, the material contained in the reaction solution, after removal of the salt waste, is a mixture of the desired ester product

(methyl 3-methoxyperfluoropropanoate), and the ketone byproduct

(di-2-methoxyperfluoroethylketone).

The process of the present invention may be conducted in a single reaction vessel, or may be conducted independently in a series of individual reaction vessels wherein at least a portion of the reaction mixture prepared in a first reaction vessel in a first step is transferred to a second reaction vessel wherein another step is conducted, and so on throughout the process. The contemplated individual reaction vessels may additionally be continuous or batch reactors. Finally, the process may be conducted in a continuous reaction system, such as a tubular reactor, wherein the reaction system contains multiple reaction zones.

ILLUSTRATIVE EMBODIMENTS

To illustrate the practice of this invention, examples of preferred embodiments are set forth below. It is not intended, however, that these examples (Examples 1-8) should in any manner restrict the scope of this invention. Some of the particularly desirable features of this invention may be seen by contrasting the characteristics of Examples 1-8 with those of controlled processes (Controls A-J) which do not possess the features of, and are not therefore embodiments of, this invention.

CONTROLS A-E AND EXAMPLES 1-3

Air and moisture are excluded from the reactions by carefully drying all glassware and assembling and operating the apparatus under a nitrogen atmosphere.

Controls A-E and Examples 1 and 2 are performed in a 2-liter 5-necked flask. The flask is placed in a dry box and loaded with sodium methoxide ("NaOCH$_3$"), 91 percent pure by Karl-Fischer titration. The flask is then placed in a fume hood and equipped with a dry ice condenser, thermowell, mechanical stirrer and addition funnel. The reactor is then loaded with tetrahydrofuran ("THF") solvent and dimethylcarbonate ("DMC") via the addition funnel.

The addition funnel is then replaced with a septum containing two ⅛" holes: one for inlet of tetrafluoroethylene ("TFE") and one for pressure measurement by a U-tube mercury manometer. The nitrogen pad on the system is shut off, and a Matheson mass flow controller is used to pass tetrafluoroethylene ("TFE") via ⅛" Teflon tubing through the reactor head-space to clear out the inerts. The reaction mixture is stirred, and the temperature shown below in Table I is maintained at the beginning of and throughout TFE addition. The TFE feed rate is adjusted so that the addition is as fast as possible without substantial pressure buildup in the system. TFE is vented for safety when the pressure in the flask exceeds 65 mm Hg.

The reaction mixture is stirred for 30 minutes while maintaining the selected temperature. The TFE gas feed line is removed and replaced with ⅛" Teflon tubing for anhydrous acid gas feed via a separate Matheson mass flow controller. HCl is then added while maintaining the temperature as also shown below in Table I, except that in Control C, H$_2$SO$_4$ is used as the acid.

Example 3 is prepared by the same procedure as set forth above for Controls A-E and Examples 1 and 2 except that a larger reaction vessel is used.

The amounts of the various reactants employed in Controls A-E and Examples 1-3, the respective temperatures of the reaction mixture during TFE and acid feed and the length of TFE and acid feed are shown below in Table I.

The crude material recovered from the flask in each run is filtered, distilled and analyzed on a Hewlett Packard 5880 gas chromatograph. The GC analysis reveals for the recovered crude material a ratio of ester product to ketone byproduct and the weight percent of the crude material represented by the ester product. This percentage of the mass of the crude material, less the salt waste, gives the moles of ester product resulting from the reaction. A percent yield of the ester product can then be calculated from a limiting number of moles of sodium methoxide, based on its purity. For example, 2.0 moles of 91 percent pure sodium methoxide would allow only a 1.82 mole theoretical yield of the ester product.

The mass of the crude material, the mass of the crude material less the salt waste, the ester product (methyl 3-methoxyperfluoropropanoate) as weight percent of the crude material, the moles of ester product, the percent yield of ester product, and the ester product to ketone byproduct (di-2-methoxyperfluoroethylketone) ratio are shown below, for Controls A-E and Examples 1-3, in Table II.

TABLE I

|  | Controls | | | | | Examples | | |
|---|---|---|---|---|---|---|---|---|
|  | A | B | C | D | E | 1 | 2 | 3 |
| NaOCH$_3$ (moles) | 2.0 | 2.0 | 2.0 | 2.0 | 2.0 | 2.0 | 1.3 | 10.0 |
| DMC (moles) | 4.8 | 4.0 | 2.5 | 4.0 | 4.0 | 4.0 | 4.0 | 20.2 |
| THF (moles) | 1.6 | 2.4 | 4.8 | 2.4 | 2.4 | 2.4 | 2.4 | 12.0 |
| TFE (moles) | 2.0 | 2.0 | 2.0 | 2.0 | 2.0 | 2.0 | 2.0 | 10.0 |
| Reaction temperature °C., during TFE feed | 30 | 30 | 25 | 40 | 20 | 10 | 10 | 10 |
| TFE addition time, hours | 3.2 | 2.8 | 2.5 | 2.8 | 2.8 | 5.3 | 2.5 | 10.0 |
| Acid (moles) | 2.0 | 2.0 | 2.0 | 2.0 | 2.0 | 2.0 | 1.3 | 10.0 |
| Reaction temperature, °C., during acid feed | 23 | 20 | 25 | 20 | 20 | 10 | 10 | 25 |
| Acid addition time, hours | 0.5 | 0.6 | 0.8 | 0.8 | 0.5 | 1.8 | 0.7 | 2.3 |

TABLE II

|  | Controls | | | | | Examples | | |
|---|---|---|---|---|---|---|---|---|
|  | A | B | C | D | E | 1 | 2 | 3 |
| Crude material, grams | 869 | 904 | 1,008 | 847 | 858 | 853 | 771 | 4,199 |
| Crude material less salt waste, grams | 758 | 788 | 784 | 739 | 748 | 744 | 672 | 3,662 |
| Ester product as weight percent | 30 | 29 | 17 | 26 | 31 | 38 | 28 | 31 |
| Ester product, moles | 1.18 | 1.19 | 0.72 | 1.00 | 1.21 | 1.48 | 0.98 | 5.94 |
| Percent yield of ester product | 65 | 65 | 39 | 55 | 67 | 81 | 83 | 65 |
| Ester/ketone weight ratio | 5/1 | 5.5/1 | 2.5/1 | 3.3/1 | 7.9/1 | 18/1 | 19/1 | 26/1 |

The results of Controls A–E and Examples 1–3 demonstrate that when a process to prepare a halogenated ester by addition of a halogenated nucleophile to a diester is run at a temperature between 15° C. and −25° C., a much higher ratio of the desired ester product to the ketone byproduct is obtained. In Controls A–E, the temperature of the reaction during the TFE gas feed ranges from 20° C. to 40° C. The highest weight ratio of ester product/ketone byproduct obtained in any of the controls (Control E) is 7.9/1. However, in Examples 1–3, the reaction temperature during TFE gas feed is below 15° C., and the resulting ester product/ketone byproduct ratio is, at a minimum, more than twice as high as that of Control E.

CONTROLS F–J AND EXAMPLES 4–8

Since water in the system will react with sodium methylate to produce caustic and methanol, all feeds should be thoroughly dried. In recognition thereof, 50.6 pounds of dimethyl carbonate ("DMC") is first mixed with 23.8 pounds of tetrahydrofuran ("THF"). This solution is then circulated through a molecular sieve bed until the water content is less than 500 weight parts per million ("ppm"). Linde 4 Angstrom (3.2 mm) molecular sieves are used for drying.

The reactor, a 20-gallon Pfaudler, is then loaded with 74.4 pounds of the dried solution of DMC and THF. This gives an equivalent of 0.56 pound/moles of DMC, or an approximate two-fold excess.

Sodium methylate is factory ordered, prepackaged in 15 pound (0.28 pound/mole) bags for ease of handling. While still sealed, one of these bags is placed inside a glove bag. The glove bag is then attached to an addition funnel that screws into a 2" valve on the top of the reactor. The glove bag is then purged with dry nitrogen for approximately 30 minutes. Once the bag has been purged, the sodium methylate bag is opened inside the glove bag and the contents are introduced into the reactor via the enclosed funnel.

After the reactor is stirring and chilled to approximately 0° C., tetrafluoroethylene ("TFE") is fed into the reactor at a rate of approximately 4 pounds/hour for a period as shown below in Table III. The total amount of TFE introduced into the reactor, and the reaction temperature throughout the TFE feed, is also shown for each run in Table III. The reaction is exothermic, and the temperature is controlled by a −10° C. Dowtherm TM cooling system and by reducing the TFE feed rate as needed. The d-limonene stabilizer is not removed from the TFE. After the TFE addition is complete, the reactants are allowed to digest for at least one hour at the selected reaction temperature.

HCl is then fed into the reactor from a ten pound gas cylinder for a period as shown in Table III. The total amount of HCl introduced into the reactor, and the reaction temperature throughout the HCl feed, is also shown for each run in Table III. The reaction mixture is agitated at approximately 300 rpm during HCl feed, and the HCL feed rate is approximately 1.5 pounds/hour. The resulting approximately 16 pounds of salt (NaCl) is held in suspension by the agitation and has a crystal size of 1–2 microns. After the reaction is complete, the system is allowed to digest for at least one hour and equilibrate at the selected temperature.

A bag filter is used to remove the solid salt crystals from the reaction mixture. The filtrate is analyzed on a Hewlett Packard 5880 gas chromatograph. The results of the following tests are shown in Table IV: weight percent of ester product (methyl 3-methoxyperfluoropropanoate) in the filtrate; weight ratio of ester product to ketone byproduct (di-2-methoxyperfluoroethylketone); pounds of ester product in filtrate; percent yield of ester product relative to amount of TFE used.

TABLE III

|  | Controls | | | | Examples | | | | |
| --- | --- | --- | --- | --- | --- | --- | --- | --- | --- |
|  | F | G | H | J | 4 | 5 | 6 | 7 | 8 |
| TFE (pounds) | 27.8 | 27.8 | 27.8 | 26.4 | 25.0 | 27.1 | 26.6 | 26.4 | 26.4 |
| Pound/mole equivalents of TFE per 0.28 pound/mole of NaOCH$_3$ | 0.99 | 0.99 | 0.99 | 0.94 | 0.89 | 0.97 | 0.95 | 0.94 | 0.94 |
| Reaction temperature, °C., during TFE feed | 13.0 | 7.0 | 2.0 | 15.0 | 5.9 | 4.1 | −0.4 | −5.7 | 0.5 |
| HCl (pounds) | 10.10 | 10.20 | 10.20 | 10.13 | 10.15 | 10.19 | 10.15 | 10.16 | 10.00 |
| Reaction temperature. °C., during HCl feed | 8.0 | 6.0 | 7.0 | 5.5 | 5.7 | 4.0 | 5.7 | 6.8 | 6.7 |

TABLE IV

|  | Controls | | | | Examples | | | | |
| --- | --- | --- | --- | --- | --- | --- | --- | --- | --- |
|  | F | G | H | J | 4 | 5 | 6 | 7 | 8 |
| Percent purity, NaOCH$_3$ | 98 | 99 | 99 | 99 | 99 | 99 | 99 | 99 | 99 |
| Weight percent of ester product in filtrate | 32 | 39 | 37 | 35 | 36 | 37 | 46 | 38 | 44 |
| Weight ratio, ester/ketone | 7.0 | 8.1 | 8.9 | 10.6 | 18.8 | 15.2 | 19.9 | 14.1 | 19.3 |
| Pounds of ester product | 22.4 | 29.0 | 32.0 | 27.9 | 31.8 | 43.1 | 50.7 | 31.5 | 46.5 |
| Percent yield of ester product | 42 | 55 | 61 | 56 | 67 | 84 | 101 | 63 | 93 |

The results of Controls F–J and Examples 4–8 demonstrate the benefits accruing from controlling temperature of reaction and amount of halogenated olefin employed when a halogenated ester is prepared by nucleophilic addition of a halogenated olefin to a diester. When a halogenated olefin is reacted with a nucleophile precursor and a diester to prepare a halogenated ester, controlling the amount of halogenated olefin employed to less than a stoichiometric equivalent, in relation to the amount of nucleophile precursor, is a causative factor in obtaining a higher percent yield and ester-product-to-ketone-byproduct ratio in the crude material resulting from the reaction. Further, running the reaction at a temperature between 15° C., and −25° C., also contributes to the obtention of a higher percent yield and ester-product-to-ketone-byproduct ratio in the crude material resulting from the reaction.

For instance, in Controls F–J, either the temperature of the reaction during TFE gas feed is not below 15° C., or an amount of halogenated olefin is used which is 99 percent or more than a stoichiometric equivalent of the amount of nucleophile precursor employed. As a result, the ester/ketone weight ratio and the percent yield of ester product is not as high in those runs as in Examples 4–8 where a reaction temperature less than 15° C., and an amount of halogenated olefin which is less than 99 percent of a stoichiometric equivalent of the amount of nucleophile precursor, are employed.

It is within the skill in the art to practice this invention in numerous modifications and variations in light of the above teachings It is, therefore, to be understood that changes may be made in the various described embodiments of this invention without departing from the spirit and scope of this invention as defined by the appended claims.

What is claimed is:

1. A process for preparing a halogenated ester comprising
   (a) contacting (i) a reaction mixture of (A) a nucleophile precursor, described by the formula M—O—Z, where M is an alkali or alkaline earth metal, and Z is a linear, branched or cyclic alkyl or alkylene radical containing 1 to 18 carbon atoms, and (B) a diester with (ii) a halogenated, ethylenically unsaturated olefin at a temperature less than about 10° C. but greater than about −25° C.,
   (b) contacting an acid with said reaction mixture, and
   (c) recovering a halogenated ester from said reaction mixture.

2. A process for preparing a halogenated ester comprising
   (a) contacting (i) a reaction mixture of (A) a nucleophile precursor, described by the formula M—O—Z, where M is an alkali or alkaline earth metal, and Z is a linear, branched or cyclic alkyl or alkylene radical containing 1 to 18 carbon atoms, and (B) a diester with (ii) less than about 0.99 mole but at least about 0.89 mole of a halogenated, ethylenically unsaturated olefin per mole of nucleophile precursor present in said reaction mixture,
   (b) contacting an acid with said reaction mixture, and
   (c) recovering a halogenated ester from said reaction mixture.

3. The process of claim 1 wherein step (a) further comprises contacting said reaction mixture with less than about 0.99 mole but at least about 0.89 mole of halogenated, ethylenically unsaturated olefin per mole of nucleophile precursor present in said reaction mixture.

4. The process of claim 1 or 3 wherein said reaction mixture is contacted with said halogenated, ethylenically unsaturated olefin at a temperature less than about 0° C. but greater than about −25° C.

5. The process of claim 2 or 3 wherein the number of moles of nucleophile precursor present in said reaction mixture is the number of 100 percent pure moles of nucleophile precursor.

6. The process of claim 1, 2 or 3 wherein, in said nucleophile precursor, Z contains halogen substituents.

7. The process of claim 1, 2 or 3 wherein said halogenated, ethylenically unsaturated olefin is described by the formula $CX_2=CX_2$, where each X is independently hydrogen, fluorine, chlorine, bromine or iodine, provided that at least one X must be fluorine.

8. The process of claim 1, 2 or 3 wherein said diester is described by the formula

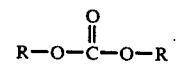

where each R is independently a linear, branched or cyclic alkyl or alkylene radical, or an aryl or arylene radical, containing 1 to 18 carbon atoms.

9. The process of claim 1, 2 or 3 wherein said nucleophile precursor is sodium methoxide.

10. The process of claim 1, 2 or 3 wherein said halogenated, ethylenically unsaturated olefin is tetrafluoroethylene.

11. The process of claim 1, 2 or 3 wherein said diester is dimethyl carbonate.

12. The process of claim 1, 2 or 3 wherein said acid is an anhydrous acid.

13. The process of claim 1, 2 or 3 wherein said acid is contacted with said reaction mixture at a temperature less than 15° C. but greater than about −25° C.